United States Patent [19]

Schaub

[11] Patent Number: 4,791,138
[45] Date of Patent: Dec. 13, 1988

[54] METHOD FOR TREATING OR PREVENTING DEEP VEIN THROMBOSIS USING LIPOXYGENASE INHIBITORS

[75] Inventor: Robert G. Schaub, Kalamazoo, Mich.
[73] Assignee: The Upjohn Company, Kalamazoo, Mich.
[21] Appl. No.: 878,116
[22] Filed: Jun. 25, 1986

Related U.S. Application Data

[63] Continuation-in-part of Ser. No. 561,602, Dec. 14, 1983, abandoned.

[51] Int. Cl.⁴ .................... A61K 31/21; A61K 31/075
[52] U.S. Cl. .................................... 514/510; 514/400; 514/415; 514/419; 514/423; 514/443; 514/469; 514/718; 514/720; 514/721
[58] Field of Search ............... 514/510, 718, 720, 721, 514/400, 419, 423

[56] References Cited

U.S. PATENT DOCUMENTS

| | | | |
|---|---|---|---|
| 3,948,958 | 4/1976 | Rapoport et al. | 260/396 |
| 4,199,531 | 4/1980 | Terao et al. | 260/607 |
| 4,320,065 | 3/1982 | Dötz | 260/438 |
| 4,358,461 | 11/1982 | Maki et al. | 424/331 |
| 4,374,775 | 2/1983 | Dötz | 260/396 |
| 4,388,312 | 6/1983 | Terao et al. | 424/244 |
| 4,393,075 | 7/1983 | Terao et al. | 242/304 |

FOREIGN PATENT DOCUMENTS

| | | |
|---|---|---|
| 2802666 | 1/1978 | Fed. Rep. of Germany . |
| 7010339 | 4/1970 | Japan . |
| 1122085 | 7/1968 | United Kingdom . |

OTHER PUBLICATIONS

G. A. Higgs et al., A New Approach to Anti-Inflammatory Drugs, Biochem. Pharmacol., 28:1959-1961 (1979).
B. Samuelsson et al., Prostaglandins and Thromboxanes, Ann. Rev. Biochem., 47:997-1029 (1978).
W. D. Wulff et al., Abstracts 88 and 89, American Chemical Society Meeting, Washington, D.C. (Aug. 18-19, 1983).
K. H. Dötz et al., XXIV Synthese von Naphthol-Derivaten Aus Carbonyl-Carben-Komplexen und Alkinen: Regioselektiver Einbau Des Alkins in Das Naphthalin-Gerust, J. of Organometal. Chem., 247:187-201 (1983).
K. Buggle et al., Decomposition Products of Pyrazolines Formed from 3-Alkylthioinden-1-Ones and Diazomethane, J. Chem. Soc. Perkin Trans., I, 572-575 (1975).
K. H. Dötz, IX Carbenliganden, Carbonylliganden und Alkine Als Bausteine fur Isocyclische und Heterocyclische Systeme, J. Organomet. Chem., 140(2):177-186 (1977).
K. H. Dötz et al., Templat-Reaktionen an Chrom(0): Stereoselektive Synthese Komplexgebundener Substituierter Naphthaline, Chem. Ber., 110:1555-1563 (1977).
C. D. Snyder et al., Synthesis of Menaquinone, J. Am. Chem. Soc., 96(26):8046-8054 (1974).
F. M. Dean et al., Spirans. Part 11. A New Method for Generating o-Quinone Methides, and Its Applications to the Synthesis of Spirochromans, J. Chem. Soc., Perkin Trans.I, 2289-2294 (1977).
O. Goncalves de Lima et al., Atividade Antimicrobiana dos Compostos Intermediarios e do Produto de Sintese 7-Metoxi-3,9-Dimetil-1-Oxafenaleno, Rev. Inst. Antibiot., Univ. Recife, 5N(1/2):3-9 (1963).
K. H. Dötz et al., Templat-Reaktionen an Chrom(0): Stereoselektive Synthese Kondensierter Aromatischer Liganden aus Pentacarbonyl-Carben-Chrom-Komplexen und Alkinen, Chem. Ber., 111:2517-2526 (1978).
M. Shiraishi et al., Studies on the Synthesis of 5-Lipoxygenase Inhibitors, J. Pharm. Dyn., 7(No.5):s-95 (1984).
M. Shiraishi and S. Terao, Quinones, Part 3. Synthesis of Quinone Derivatives having Ethylenic and Acetylenic Bonds: Specific Inhibitors of the Formation of Leukotrienes and 5-Hydroxyicosa-6,8,11,14-Tetraenoic Acid (5-HETE), J. Chem. Soc. Perkin Trans.I, 1591-1599 (1983).

Primary Examiner—Frederick E. Waddell
Attorney, Agent, or Firm—Lawrence T. Welch; Martha A. Cox

[57] ABSTRACT

The present invention provides a novel methoda for preventing deep vein thrombosis comprising the administration of lipoxygenase inhibitors of Formula I

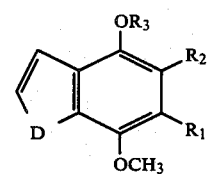

5 Claims, No Drawings

METHOD FOR TREATING OR PREVENTING DEEP VEIN THROMBOSIS USING LIPOXYGENASE INHIBITORS

CROSS-REFERENCE

This invention is a continuation-in-part of patent application, Ser. No. 561,602, filed Dec. 14, 1983, now abandoned.

BACKGROUND OF THE INVENTION

The present invention provides a new use of known compositions. More particularly, the present invention provides a method for the prevention of venous thrombosis using lipoxygenase inhibitors.

Thrombosis of the lower limb deep veins, or deep vein thrombosis (DVT) is a frequent occurrence after major surgery, massive trauma, myocardial infarction, neoplasia, and pregnancy. (See, e.g., Bell, et al., Am. Heart J. 103: 239 (1982), Coon, Ann. Surg. 186: 149 (1977), and Kakkar, et al., Am. J. Surg. 120: 527 (1972).) While DVT may not always be dangerous, growth of thrombi and their subsequent embolization may become life threatening if these emboli lodge in the pulmonary circulation. It has been estimated that 11–20% of all venous thrombi will embolize. (See, Freeman, et al., N. Engl. J. Med. 272: 1270 (1965) and Salzman, et al., Am. Surg. 93: 207 (1980).) Therapeutic interventions for prevention of venous thrombosis, while available, have not been demonstrated to be completely effective or without significant side effects in the high risk patient. Low dose heparin is effective in the prevention of DVT in the general surgical patient. However, low dose heparin appears to be without significant effect in the prevention of DVT in patients in orthopedic surgical procedures, in trauma cases, following colorectal surgery, and in post myocardial infarct patients. See, e.g., Bell, supra, Freeman, supra, Gallus, et al., N. Engl. J. Med. 288: 454 (1973), Kass, et al., J. Urol. 120: 239 (1982), Salzman, et al., N. Engl. J. Med. 284: 287 (1971), and French, et al., The Lancet, 1 (8231): 1212 (1981). Warfarin when given prophylactically can significantly reduce DVT in highest risk patients, but bleeding is a frequent complication of oral anti-coagulation (see, Salzman, Am. Surg. 93: 207 (1980)). Fatal hemorrhage has been reported in 1.8 percent of the patients on Warfarin. See, Gallus, et al., Thromb. Hemostasis (2: 291 (1976). Low molecular weight dextran therapy for DVT is complicated by the possibility of anaphylaxis, pulmonary edema subsequent to volume overload, and renal damage. See, Bell, supra and Salzman, supra. Aspirin has proved effective in high risk male patients but not in high risk female patients. See, Salzman, supra at Harris, et al., N. Engl. J. Med. 297: 1246 (1977).

In mammalian metabolism, arachidonic acid is transformed to 12-L-hydroproxy-5,8,10,24-eicosatetraenoic acid by the action of 14-lipoxygenase. See, Hamberg, et al., Proc. Nat. Acad. Sci. 71: 3400–3404. Similarly, 5-lipoxygenase transforms arachidonic acid into 5-S-hydroperoxy-6-8,11,14-eicosatetraenoic acid. Doig, et al., Prostaglandins: 1007–1009 (1980) and Lynn, et al., J. Clin. Invest. 70: 1058 (1982) disclosed that 5-lipoxygenase inhibitors block platelet thrombus formation.

It has been suggested that leukocytes contribute to the initiation of venus thrombosis by producing endothelial damage. See, e.g., Stewart, et al., Am. J. Path. 75: 507 (1974). Arachidonic acid, when metabolized by lipoxygenase, produces mono-, di-, and tri-hydroxyeicosatetraenoic acids (HETE's). Recent evidence indicates that the substances (leukotrienes) are important mediators of the inflammatory process, stimulating the chemoattraction of leukocytes and their adhesion to the vascular endothelium. See Agges, et al., Biochem. Pharmacol. 28: 1959 (1979), and Sammuelsson, et al., Ann. Rev. 47: 997 (1978). The compound 5-12-di-HETE (leukotriene B$_4$) is a very potent activator. See, Ford-Hutchinson, et al., Nature 286: 264 (1980). Two other leukotrienes, leukotrienes C$_4$ and D$_4$ also appear to have a role in the chemotactic response. Both of these substances have been found to induce vasoconstriction and to increase vascular permeability. See, Peck, et al., Prostaglandins 21: 315 (1981).

Certain inhibitors of lipoxygenase are known. Thus, Hammarstrom, Biochim. Biophys. Acta. 487: 517 (1977) discloses the lipoxygenase inhibitory activity of 5,8,11-eicosatriynoic acid. Vanderhoek, et al., J. Biol. Chem. 255: 5996 (1980) discloses 15-hydroxy-5,8,11,13-eicosatetraenoic acid as a selective inhibitor of platelet lipoxygenase. Seckiya, et al., Biophys. Res. Comm. 105: 1090 (1982) reports that baicalein is a selective inhibitor of platelet lipoxygenase, while Bokoch, et al., J. Biol. Chem. 256: 5317 (1981) states that nordihydroguaiaretic acid (NDGA) is also a lipoxygenase inhibitor. Certain quinone compounds are disclosed as lipoxygenase inhibitors in U.S. Pat. No. 4,393,075.

INFORMATION DISCLOSURE

Many lipoxygenase inhibitors are known, as described above. It is also theorized that leukotrienes stimulate the chemoattraction of leukocytes and their adhesion to the vascular endothelium. See Agges, supra and Sammuelsson, supra.

SUMMARY OF THE INVENTION

The present invention particularly provides:

A method for preventing deep vein thrombosis (DVT) in a mammal susceptible to said DVT comprising administering to said mammal an amount effective to prevent said DVT of a lipoxygenase inhibitor.

By "deep vein thrombosis" (DVT) is meant the thrombosis (clot formation) of the lower limb deep veins (e.g., popliteral, femoropopliteal, and femoral veins). Such thrombosis is frequently a result of major surgery, massive trauma, myocardial infarction, neoplasia, and pregnancy. The term "deep vein thrombosis" or "DVT" is meant to encompass the thrombosis resulting from these or any other causes. A "mammal susceptible to said DVT" is thus a mammal undergoing or likely to undergo any of these diseases or conditions. Such mammals are readily determined by physicians or veterinarians of ordinary skill in the art.

By "lipoxygenase inhibitor" is meant any pharmaceutically acceptable substance which is effective to inhibit the action of any lipoxygenase in mammalian metabolism. These include: 5,8,11-eicosatriynoic acid (see, Hammarstrom, supra); 15-hydroxy-5,8,11,13-eicosatetraenoic acid (see, Vanderhoek, supra); baicalein (see, Seckiya, supra); nordihydroguaiaretic acid (NDGA) (see, Bockoch, supra); certain quinones (see, U.S. Pat. No. 4,393,075); Vitamin E and related tocopherols (see U.S. Pat. No. 4,386,072); certain structural analogs of 5,6-dihydro-PGI$_1$ (see, U.S. Pat. No. 4,294,759); benoxaprofen and similar nonsteroidal antiinflammatory compounds (see, U.S. Pat. No. 4,355,029); and certain novel substituted naphthalenes, indoles, benzofurans, benzothiophenes of the Formula I (see U.S. Pat. No. 4,737,519, which is hereby incorporated by reference herein). All of these and any other pharmaceutically acceptable lipoxygenase inhibitors are employed in the method of this invention. All of these compounds are well known and readily available, may be prepared by means well known in the art, may be prepared as described in U.S. Pat. No. 4,737,519 herein, or may be prepared as described in the U.S. patents described above, the specifications of which are incorporated by reference herein.

Thus, the present invention particularly provides for a method for preventing deep vein thrombosis (DVT) in a mammal susceptible to said DVT comprising administering to said mammal an amount effective to prevent said DVT of a lipoxygenase inhibitor, wherein the lipoxygenase inhibitor is a compound of the Formula I, wherein $R_1$ and $R_2$ are the same or different and are
  (a) hydrogen,
  (b) $(C_1-C_{10})$alkyl,
  (c) $(C_2-C_{10})$alkenyl, or
  (d) PhX;
wherein (PhX) is phenyl substituted by zero to 3 of the following:
  (a) $(C_1-C_4)$alkyl,
  (b) chloro,
  (c) fluoro,
  (d) bromo,
  (e) nitro,
  (f) trifluoromethyl; or
  (g) $OR_4$;
wherein D is
  (a) —CH=CH—,
  (b) =N(CH_3),
  (c) —S—,
  (d) —O—;
wherein $R_3$ is
  (a) $CH_3$—C(O)—,
  (b) hydrogen;
  (c) —C(O)—$(CR_{17}R_{18})_m$—$(CH_2)_n$—$NR_{14}R_{15}$,
  (d) —C(O)—AA, or
  (e) —C(O)—PhX—$NH_2$;
wherein m is 1, 2, 3, or 4;
wherein n is 0, 1, 2, 3, 4, or 5;
wherein —C(O)AA is the acyl portion derived from any naturally occurring alpha-amino acid;
wherein $R_{14}$ and $R_{15}$ are the same or different and are:
  (a) hydrogen,
  (b) $(C_1-C_{10})$alkyl,
  (c) —C(O)$R_{16}$,
  (d) —C(O)—PhX, or
  (e) —PhX;
with the proviso that $R_{14}$ and $R_{15}$ are other than hydrogen when n is zero;
wherein $R_{16}$ is $(C_1-C_4)$alkyl;
wherein $R_{17}$ and $R_{18}$ are the same or different and are:
  (a) hydrogen,
  (b) $(C_1-C_{10})$alkyl,
  (c) —$CH_2$—PhX, or
  (d) —PhX;
with the proviso that each occurrence of $R_{17}$ and $R_{18}$ may be the same or different; wherein PhX—$NH_2$ is an amino-substituted phenyl group additionally substituted by zero to 3 of the following:
  (a) $(C_1-C_4)$alkyl,
  (b) chloro,
  (c) fluoro,
  (d) bromo,
  (e) nitro,
  (f) trifluoromethyl, or
  (g) $OR_4$;
wherein $R_4$ is
  (a) hydrogen, or
  (b) $(C_1-C_4)$alkyl;
with the following provisos
  (1) when D is —CH=CH— or =N(CH_3), $R_3$ is not hydrogen;
  (2) when D is —CH=CH— and one of $R_2$ and $R_1$ is hydrogen or methyl, the other is not hydrogen or methyl;
  (3) when D is =N(CH_3), $R_1$ and $R_2$ are not phenyl; and
  (4) when D is —CH=CH— and $R_2$ is phenyl, $R_1$ is other than hydrogen;
or a pharmacologically acceptable acid addition salt thereof, when $R_3$ is
  (c) —C(O)—$(CR_{17}R_{18})_m$—$(CH_2)_n$—$NR_{14}R_{15}$,
  (d) —C(O)—AA, or
  (e) —C(O)—PhX—$NH_2$.

By "prevention" is meant the total or partial avoidance of clot formation in the deep veins of a mammal.

By —C(O)—AA is meant the acyl part of an amino acid including the naturally-occurring acids such as: glycine, alanine, valine, leucine, isoleucine, phenylalanine, lysine, proline, tryptophan, methionine, serine, threonine, cysteine, tyrosine, asparagine, glutamine, aspartic acid, glutamic acid, arginine, ornithine, and histidine, and synthetic derivatives thereof. These compounds may be in L or D configuration and are well known and readily available to those skilled in the art. Thus, AA—COOH would represent the amino acids themselves.

The present invention includes the treatment of each of various mammalian species, including humans. With respect to non-humans, the present invention is particularly and especially concerned with treating domesticated animals, for example, cattle, dogs, cats, and swine. Humans are the most preferred mammals to be treated by the methods of this invention.

Any convenient route of administration is employed. Thus, oral formulation and oral administration is, for example, the preferred route for use in humans although parenteral (e.g., intraveneous, intraperitoneal, and intramuscular) administration is also employed.

The dosage regimen for the compounds used in accord with this invention will depend on a variety of factors, including the type, age, weight, sex, and medical condition of the mammal, and most importantly on the risks and probable consequences of deep vein thrombosis. It is within the skill of the attending physician or veterinarian to determine the risks of deep vein thrombosis, and to prescribe an effective amount of the lipoxygenase inhibitors claimed herein. When lipoxygenase inhibitors such as 1-acetoxy-2-butyl-4-methoxynaphthalene or 1-acetoxy-2,3-diethyl-4-methoxynaphthalene are used, the dosage is in the range of about 0.01 to about 1 mg/kg/minute by intravenous infusion, or about 0.1 to about 50 mg/kg/day by oral administration. Equivalent dosages for other routes of administration are also employed. Similarly, when other lipoxygenase inhibitors are employed, equipotent doses are administered based on the compound's comparative potency as demonstrated in the standard laboratory tests set forth as Examples 1 and 2 below.

It is preferred to use the compounds set forth in U.S. Pat. No. 4,737,519 herein. Most preferred for use in this method are 1-acetoxy-2-n-butyl-4-methoxynaphthalene; 1-acetoxy-2,3-diethyl-4-methoxynaphthalene; and L-Valine, 2-n-butyl-4-methoxynaphth-1-yl ester, hydrochloride.

DESCRIPTION OF THE PREFERRED EMBODIMENTS

The operation of the present invention is seen more fully by the example given below.

EXAMPLE 1

Nordihydroguaiaretic acid (NDGA)

A. Preparation of a pure suspension of leukocytes

Leukocyte suspensions were obtained using a modification of the method of Henson, J. Immun. 107: 1535 (1971). Seven domestic short hair adult cats (4-5 kg) were anesthesized with sodium thiamyl (25 mg/kg i.v.) (Parke-Davis, Morris Plains, NJ), and 30 ml of blood was drawn by heart puncture into 1/7 volume of acid citrate dextrose (ACD). The blood was centrifuged at 150G (850 rpm) for 10 minutes at room temperature using a Beckman TJ-6 Refrigerated Centrifuge. The supernatant, which was platelet-rich plasma (PRP), and the buffy coat were removed using a polyethylene Pasteur pipette (Centaur Chemical Co., Stamford, CN). (This supernatant was centrifuged for 10 minutes at 1800G at 4° C. to remove all suspended particles, and the plasma was saved in a refrigerator). The red blood cells and leukocytes were suspended in pyrogen free saline containing 2.5% gelatin (Difco Laboratories, Detroit, MI). The solution was mixed by inversion, and the erythrocytes were allowed to sediment at 1G for 30 minutes at 37° C. A white cell button was obtained by centrifuging the supernatant at 400G (1400 rpm) for 10 minutes at room temperature. The leukocyte button was resuspended in 0.87% ammonium chloride in water (pH 7.2) to cause lysis of the remaining red cells. After 5 minutes the cells were centrifuged at 200G (1000 rpm) for 10 minutes at 4° C. The supernatant was removed, and the cells were washed with albumin Tyrode's solution (2.5%). The cells were centrifuged down as before and resuspended in albumin Tyrode's solution (2.5%). In order to maintain cell viability, the leukocytes were kept on ice until used.

Before being radioactively labeled the cells were counted and tested for viability to insure that viable cells had been isolated. White cell counts were made using a Neubauer Hemocytometer (American Optical, Buffalo, NY). Viability was tested by trypan blue exclusion.

B. Preparation of reaction medium

Acid citrate dextrose was prepared with 80 mg of citric acid, 224 mg of anhydrous sodium citrate, and 120 mg of anhydrous dextrose per 10 ml of solution.

The saline used (Isotonic Buffered Saline, American Scientific Products, McGraw Park, IL) contained, per liter: 180 mEq Na, 5.1 mEq K, 153 mEq Cl, 1.0 mmol EDTA, and trace amounts of 2-phenoxyethanol.

Tyrode's solution was made by adding, per liter: 200 mg $CaCl_2$, 100 mg $MgCl_2(6H_2O)$, 200 mg KCl, 8000 mg NaCl, 50 mg $NaH_2PO_4(H_2O)$, 100 mg glucose, and 1000 mg $NHCO_3$. (The $NHCO_3$ was added last until a pH of 7.35 to 7.40 was achieved). Bovine albumin powder (Armour Pharmaceutical Co., Kankakee, IL) was added 2.5% by weight.

All solutions were sterilized in 115 Nalgene sterilization filter units (Nalge Co., Rochester, NY) with 0.20 micron pores.

C. Radioactive labeling of leukocytes

Indium-111 was purchased as the hydrochloride from New England Nuclear Corporation and converted to the membrane soluble oxine using a modification of the method of Thakur (1977). Approximately 150 microcuries in Indium-111 oxine (2.0 mCi/300 µl) were added to leukocytes suspended in 2 to 4 ml of albumin Tyrode's solution (2.5%) and allowed to incubate 20 minutes. The solution was centrifuged at 850G (2000 rpm) for 5 minutes at 4° C. The button was resuspended in albumin Tyrode's solution (2.5%) and centrifuged as above. After a final washing in chilled plasma the cells were suspended in 2.000 or 4.000 ml of plasma, depending on the quantity of cells isolated.

D. Treatment of leukocytes with the leukotriene inhibitor NDGA

The leukocyte suspensions of four cats were treated with nordihydroguaiaretic acid (NDGA; 4,4'-(2,3-dimethyl tetramethylene)dipyrocatechol, 100 µg/ml). This compound is a potent inhibitor of the lipoxygenase enzyme (Bokoch, 1981).

White cell count and viability were again tested and recorded at this point. Also, a measured volume of the suspension was placed in a 12 by 75 mm test tube to serve as a standard.

E. Surgical procedure

Each cat was anesthesized intravenously with Nembutal (500 mg pentobarbital sodium/ml) (Abbott Laboratories, North Chicago, IL) and tied in the dorsal recumbant position. The ventral side of the neck was sheared with clippers and then shaved with a razor blade. The area was sterilized using Betadine soap and betadine with 10% iodine. After scrubbing and donning sterile gloves, the surgical area was carefully covered with sterile towels and a drape.

A 6 to 8 cm longitudinal incision was made medial to each external jugular vein. Connective tissue, fat, and adventitia were restricted away so as to expose the jugular veins. Care was taken in ligating and detaching all side branches from a 3 to 4 cm section of the vessel (4-0 Silk, American Cyanamide Co., Pearl River, NY). A ⅜ inch 26 gauge needle with a bent tip was inserted into the cranial end of the isolated section of the vessel, and suture (4-0 Silk) was used to hold the needle in position. The vessel was flushed with sterile saline and tied off proximal to the heart. All fluid was extracted from the vessel and approximately 0.2 ml of the labeled leukocyte solution was injected. Upon removal of the needle, the cranial end was tied off, and the distended vessel was allowed to sit for one hour. At the end of one hour the vessel was removed and placed in Tyrode's solution. The wound was closed using a continuous lock stitch (2-0 or 3-0 Dexon, absorbable, Davis and Geck, Inc., Manati, PR).

F. Preparation of the vessel for radioactive counting

Suture and excess tissue were removed from the jugular vein. Half of the vessel was weighed, and radioactivity of the specimen was counted in a Packard Gamma Scintillation Spectrometer. For each vessel the following computations were made: total counts per minute (cpm), cpm/gm of tissue, total number of white cells adhered, and number of white cells adhered/gm of tissue. The other half of the vessel was opened with a longitudinal cut and mounted luminal side up on a cork board to be prepared for scanning electron microscopy.

G. Preparation of the vessel for SEM

One-half of each jugular vein was prepared for scanning electron microscopy (SEM) whenever sufficient tissue was available for both counting and microscopy. Sections of jugular vein were tied onto glass microscope slides using 4-0 Dexon and immersed in 2.5% glutaraldehyde in Tyrode's solution. Samples were rinsed 3 times in Tyrode's solution and post-fixed overnight in 1% osmium tetroxide. After rinsing 3 times with distilled water, tissues were dehydrated in absolute ethanol 2 times for one hour each and once overnight. Ethanol was substituted by amyl acetate, and the samples were permitted to air dry. The veins were mounted on stubs (Ted Pella, Inc., Tustin, CA), gold coated on a Denton DV-502 Vacuum Evaporator, and examined on a Cambridge Stereoscan 150 Scanning Electron Microscope for deposition of leukocytes on the luminal surface.

H. Preparation of leukocyte suspension for TEM

Two leukocyte suspensions were fixed for transmission electron microscopy (TEM) to verify the purity and types of leukocytes found in the isolated material. Briefly, 1 ml of suspension was diluted with 10 ml of 1% glutaraldehyde in Tyrode's buffer and allowed to fix for 1 hour. The cells were washed 2 times in Tyrode's buffer and post-fixed in 1% osmium tetroxide for 15 minutes. The suspensions were washed in Tyrode's solution, dehydrated in absolute ethanol, substituted with propylene oxide, and infiltrated with Medcast/Araldite (Ted Pella, Inc., Tustin, CA). Tissues were sectioned with a diamond knife (Dupont Instruments, Bear, DE) on a Porter/Blum MT2-B Ultra-Microtome. All sections were stained with uranyl acetate and lead citrate and examined on a Phillips 301 Transmission Electron Microscope.

I. Results

Table 1 shows the number of leukocytes deposited per gram of tissue for each jugular vein. Values for both the treated and untreated groups appear relatively consistent with the exception of those for cat 466, both of which are significantly higher than the corresponding values for other treated vessels. In general deposition is shown to occur in the untreated group, but this can best be verified by SEM analysis.

Vessels prepared for SEM were each graded for four conditions: (1) white cell adhesion, (2) white cell invasion, (3) endothelial damage, and (4) fibrin deposition, as explained in Table 2. The results are summarized in Tables 3 and 4. Excellent correlations can be seen between the calculated (Table 1) and observed results (Tables 3 and 4). Upon SEM analysis untreated vessels showed greater amounts of leukocyte adhesion, leukocyte invasion, endothelial damage, and fibrin deposition compared to treated vessels.

Untreated vessels typically exhibited extensive white cell adhesion and invasion resulting in total destruction of the luminal surface and exposure of the subendothelium. In areas of greatest disruption fibrin deposits were frequently present in varying amounts. Under high magnification (2000X) white cells could be clearly identified and it was evident that their normally smooth surfaces had become ruffled and distorted, a sign of activation. In some areas fibrin deposits were so extensive that leukocytes were literally buried in fibrin, and abnormally high magnification (2000X) was required to differentiate between normal endothelium and regions of thick fibrin deposits.

In most of the treated vessels normal and intact endothelium comprised the major portion of the lumen. At high enough magnification (1000X) raised nuclei and intracellular junctions were readily visible. Some samples exhibited mild distortion of the endothelium including splitting, craters, and dissociation of nuclei from their cells; however, this seemed to occur in the absence of leukocyte deposition. Occasionally, a treated vessel whose surface was grossly intact and free of leukocytes would display extensive leukocyte deposition in selective areas such as regions adjacent to valve pockets, side branches, and luminal ridges. The opportunity for blood stasis is greater in these areas, and thus the chance of leukocyte deposition in response to leukotactic gradients is higher.

Several of the treated vessels did exhibit extensive regions of leukocyte adhesion, leukocyte invasion, endothelial damage, and fibrin deposition. The extent to which each of these occurred in treated vessels varied so greatly that it is possible to deduce the probable sequence in which these events normally occur. Some areas clearly showed extensive adhesion and invasion rendering the surface extremely lumpy and uneven as emigrating leukocytes forced up the endothelium. However, the endothelium in these regions was grossly intact, although somewhat distorted, and no fibrin deposits were evident. In other regions the endothelium was severely damaged, although no fibrin deposition had occurred. Large portions of intact endothelium remained through which leukocytes apparently had yet to emigrate. Finally, there were regions in which the endothelium had been either removed or entirely damaged by the action of emigrating leukocytes. Often basement membrane was visible, as were fibrin deposits.

EXAMPLE 2

Treatment of deep vein thrombosis using 2,3-diethyl-4-methoxy-1-naphthalenol, acetate Nine adult domestic short hair cats weighing 4.5–5 kg were anesthetized with sodium pentabarbital (25–30 mg/kg i.v.). The neck area was prepared for a sterile cut down procedure and the jugular veins were exposed. After exposure of the veins each animal was injected with epsilon amino caproic acid (eaca) to inhibit plasminogen activation (2.5 grams i.v. in Tyrode's solution). This was done to reduce the normally high active feline fibrinolytic mechanism and thus reduce lysis of fibrin thrombi which might form in the vessel. Six of the cats were also treated with 2,3-diethyl-4-methoxy-1-naphthalenol, acetate. Three of the cats were given 1 mg/kg i.v. and 3 of the cats were treated with 5 mg/kg i.v. prior to venous occlusion. The jugular veins were carefully dissected free of surrounding connective tissue and the vein was ligated at the thoracic inlet with 3-0 dexon. The skin incision was closed and the animals were maintained in surgical anesthesia for two hours. At the end of the 2 hour waiting period, the jugular veins were exposed again. A 25 gauge butterfly needle was positioned into the lumen and blood was flushed out of the vein with heparinized Tyrode's solution (1U heparin/ml). The veins were tied off and removed under physiologic pressure. The vessels were immediately immersed in a 2.5% glutaraldehyde solution prepared in Tyrode's solution for fixation. The veins were fixed overnight at 5° C., postfixed in 1% osmium tetroxide overnight, dehydrated in ethanol and substituted by amyl acetate. All veins were critical point dried from carbon dioxide using a Denton DCP-1 critical point drying apparatus. The veins were mounted on stubs, gold coated on a Denton DV-502 modified vacuum evaporator and examined on a Cambridge Stereoscan 150 scanning electron microscope.

Two hours of jugular vein stasis following the trauma of dissection caused massive white cell adhesion to and migration under the venous endothelium of non-treated cats and produced sloughing of the endothelium and exposure of the basement membrane. This damage was sufficient to initiate thrombosis. Many of the exposed areas of basement membrane had adherent platelets. The platelets were adherent as monolayers or as aggregates. In some areas fibrin was found deposited on the endothelium or exposed basement membrane. Leukocytes were occasionally associated with the fibrin.

2,3-Diethyl-4-methoxy-1-naphthalenol, acetate had a dose dependent effect on the vascular changes described above. The 1 mg/kg dose did not reduce leukocyte adhesion or migration. Most of the surface of all the veins examined in this group had multiple aggregates of leukocytes visible under the intact endothelium. Although leukocyte migration was not inhibited, leukocyte release of hydrolytic enzymes and production of superoxide's was apparent inhibited. Few areas with detached endothelial cells or exposed basement membrane were found in this group.

The 5 mg/kg dose had an even greater inhibitory effect on leukocyte mediated damage. In this group only patchy areas of adherent leukocytes were observed. In most of these areas leukocytes were also found under the endothelium. It was only in these areas, however, that endothelial cell loss and platelet deposition were observed. The numbers of adhering and migrating leukocytes found in this group appeared to be less than in either the control or 1 mg/kg treated group. With the exception of one vein, approximately half or more of the vascular surface had an intact endothelial cell cover with few adherent leukocytes. Only occasional small areas of fibrin deposition were found in this group.

TABLE 1

| Cat # | Vessel | Number of Cells per Gram of Tissue* |
|---|---|---|
| (Untreated) | | |
| 334 | left | 41.4 |
| | right | 18.6 |
| 332 | left | 14.8 |
| | right | 17.9 |
| 325 | left | 64.3 |
| | right | 22.0 |
| | | Mean = 29.8 |
| | | S.E. = 7.91 |
| (Treated) | | |
| 398 | left | 3.07 |
| | right | 4.99 |
| 228 | left | 7.39 |
| 466 | left | 17.3 |
| | right | 56.1 |
| 457 | left | 7.73 |
| | right | 6.04 |
| | | Mean = 14.7 |
| | | S.E. = 7.12 |
| | | p. = 0.0321** |
| | excluding 466: | Mean = 5.84 |
| | | S.E. = 0.85 |

TABLE 1-continued

| Cat # | Vessel | Number of Cells per Gram of Tissue* |
|---|---|---|
| | | p. = 0.0062** |

*Values expressed in millions.
**Wilcoxon's ranksum test for pair-wise comparisons
TABLE 1. LEUKOCYTE DEPOSITION ON JUGULAR VEINS OF UNTREATED AND NDGA-TREATED CATS: The cats in both groups were held under anesthesia for approximately the same length of time, and the veins were exposed, perfused, and processed by the same methods. The only variable was the presence of NDGA in the leukocyte suspensions used for the treated group.

TABLE 2

| Description | Ratings |
|---|---|
| 1. extent | none |
| | rare |
| | sparse |
| | moderate |
| | heavy |
| 2. arrangement | patchy |
| | uniform |
| 3. amount of luminal surface involved | estimated % |

TABLE 2. DESCRIPTION OF LUMINAL SURFACE OF JUGULAR VEINS AS SEEN UNDER SEM: All ratings were made as relative estimates by the same individual to insure greatest possible accuracy.

TABLE 3

| Cat # | Vessel | White Cell Adhesion | White Cell Invasion | Endothelial Damage | Fibrin Deposition |
|---|---|---|---|---|---|
| 325 | left | heavy uniform 90% | heavy uniform 90% | heavy uniform 90% | moderate patchy 15% |
| 334 | right | sparse patchy 25% | sparse patchy 25% | moderate patchy 25% | sparse patchy 5% |
| 334 | left | moderate patchy 50% | moderate patchy 50% | moderate patchy 50% | sparse patchy 10% |
| 332 | right | moderate uniform 80% | moderate uniform 80% | heavy uniform 80% | sparse patchy 10% |

TABLE 3. SEM ANALYSIS OF UNTREATED JUGULAR VEINS: For any given animal the descriptions for white cell adhesion, white cell invasion, and endothelial damage are comparable, indicating a close relationship between these characteristics. Fibrin deposition, although minimal in some cases, was at least exhibited by all the vessels.

TABLE 4

| Cat # | Vessel | White Cell Adhesion | White Cell Invasion | Endothelial Damage | Fibrin Deposition |
|---|---|---|---|---|---|
| 398 | left | sparse uniform 90% | sparse patchy 20% | rare patchy <1% | rare patchy 1% |
| 398 | right | sparse patchy 20% | sparse patchy 20% | rare patchy <1% | rare patchy <1% |
| 457 | right | rare patchy <1% | none — — | none — — | none — — |
| 228 | left | sparse patchy 10% | none — — | none — — | none — — |
| 466 | left | heavy uniform 90% | heavy uniform 90% | moderate uniform 90% | none — — |
| 466 | right | heavy uniform 90% | heavy uniform 90% | heavy uniform 90% | moderate uniform 15% |

TABLE 4. SEM ANALYSIS OF NDGA-TREATED JUGULAR VEINS: The results appear far less consistent for this group than for the untreated group. Values of 1% or less are common throughout the table, especially in the areas of endothelial damage and fibrin deposition, two important precursors to thrombus formation.

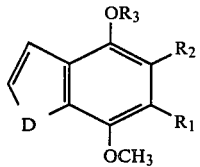

I claim:

1. A method for preventing deep vein thrombosis (DVT) in a mammal susceptible to said DVT comprising administering to said mammal an amount effective to prevent said DVT of a lipoxygenase inhibitor, wherein the lipoxygenase inhibitor is a compound of the Formula I

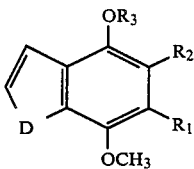

wherein $R_1$ and $R_2$ are the same or different and are
  (a) hydrogen,
  (b) $(C_1-C_{10})$alkyl,
  (c) $(C_2-C_{10})$alkenyl, or
  (d) PhX;
wherein (PhX) is phenyl substituted by zero to 3 of the following:
  (a) $(C_1-C_4)$alkyl,
  (b) chloro,
  (c) fluoro,
  (d) bromo,
  (e) nitro,
  (f) trifluoromethyl; or
  (g) $OR_4$;
wherein D is
  (a) —CH=CH—,
wherein $R_3$ is
  (a) $CH_3$—C(O)—,
  (b) hydrogen;
  (c) —C(O)—$(CR_{17}R_{18})_m$—$(CH_2)_n$—$NR_{14}R_{15}$,
  (d) —C(O)—AA, or
  (e) —C(O)—PhX—$NH_2$;
wherein m is 1, 2, 3, or 4;
wherein n is 0, 1, 2, 3, 4, or 5;
wherein —C(O)AA is the acyl portion derived from any naturally occurring alpha-amino acid, wherein $R_{14}$ and $R_{15}$ are the same or different and are:
  (a) hydrogen,
  (b) $(C_1-C_{10})$alkyl,
  (c) —C(O)$R_{16}$,
  (d) —C(O)—PhX, or
  (e) —PhX;
with the proviso that $R_{14}$ and $R_{15}$ are other than hydrogen when n is zero;
wherein $R_{16}$ is $(C_1-C_4)$alkyl;
wherein $R_{17}$ and $R_{18}$ are the same or different and are:
  (a) hydrogen,
  (b) $(C_1-C_{10})$alkyl,
  (c) —$CH_2$—PhX, or
  (d) —PhX;
with the proviso that each occurrence of $R_{17}$ and $R_{18}$ may be the same or different; wherein PhX—$NH_2$ is an amino-substituted phenyl group additionally substituted by zero to 3 of the following:
  (a) $(C_1-C_4)$alkyl,
  (b) chloro,
  (c) fluoro,
  (d) bromo,
  (e) nitro,
  (f) trifluoromethyl, or
  (g) $OR_4$;
wherein $R_4$ is
  (a) hydrogen, or
  (b) $(C_1-C_4)$alkyl;
with the following provisos
  (1) $R_3$ is not hydrogen;
  (2) and one of $R_2$ and $R_1$ is hydrogen or methyl, the other is not hydrogen or methyl;
  (3) when $R_2$ is phenyl, $R_1$ is other than hydrogen; or a pharmacologically acceptable acid addition salt thereof,
when $R_3$ is
  (c) —C(O)—$(CR_{17}R_{18})_m$—$(CH_2)_n$—$NR_{14}R_{15}$,
  (d) —C(O)—AA, or
  (e) —C(O)—PhX—$NH_2$.

2. The method of claim 1 wherein said mammal is a human.

3. The method of claim 2 wherein the compound is 1-acetoxy-2-butyl-4-methoxynaphthalene; or 1-acetoxy-2,3-diethyl-4-methoxynaphthalene.

4. The method of claim 2 wherein $R_3$ is
  (a) —C(O)—$(CR_{17}R_{18})_m$—$(CH_2)_n$—$NR_{14}R_{15}$,
  (b) —C(O)—AA, or
  (c) —C(O)—PhX—$NH_2$.

5. The method of claim 4 wherein the compound is L-Valine, 2-n-butyl-4-methoxynaphth-1-yl ester, hydrochloride.

* * * * *